US011642013B2

(12) United States Patent
Shijo

(10) Patent No.: US 11,642,013 B2
(45) Date of Patent: May 9, 2023

(54) METHOD OF PRODUCING ENDOSCOPE FLEXIBLE TUBE AND METHOD OF PRODUCING ENDOSCOPE

(71) Applicant: HOYA CORPORATION, Tokyo (JP)

(72) Inventor: Yoshihisa Shijo, Saitama (JP)

(73) Assignee: HOYA CORPORATION, Tokyo (JP)

( * ) Notice: Subject to any disclaimer, the term of this patent is extended or adjusted under 35 U.S.C. 154(b) by 677 days.

(21) Appl. No.: 16/489,823

(22) PCT Filed: Mar. 19, 2018

(86) PCT No.: PCT/JP2018/010674
§ 371 (c)(1),
(2) Date: Aug. 29, 2019

(87) PCT Pub. No.: WO2018/180652
PCT Pub. Date: Oct. 4, 2018

(65) Prior Publication Data
US 2019/0380560 A1    Dec. 19, 2019

(30) Foreign Application Priority Data
Mar. 31, 2017    (JP) .............................. JP2017-072400

(51) Int. Cl.
*A61B 1/005*    (2006.01)
*A61B 1/00*     (2006.01)
(Continued)

(52) U.S. Cl.
CPC .......... *A61B 1/0051* (2013.01); *A61B 1/0011* (2013.01); *A61B 1/00071* (2013.01); *A61L 29/08* (2013.01); *B29L 2023/007* (2013.01)

(58) Field of Classification Search
CPC . A61B 1/0011; A61B 1/00071; A61B 1/0051; A61L 29/08
See application file for complete search history.

(56) References Cited

U.S. PATENT DOCUMENTS 1,706,161 A * 3/1929 Hollnagel .......... A61B 1/00071
                                              607/93
2,541,064 A * 2/1951 Irons ....................... B29C 48/08
                                              264/564
(Continued)

FOREIGN PATENT DOCUMENTS

JP    H02-131738 A    5/1990
JP    H11-262468 A    9/1999
(Continued)

OTHER PUBLICATIONS

Search Report issued in International Bureau of WIPO Patent Application No. PCT/JP2018/010674, dated May 15, 2018.

*Primary Examiner* — John P Leubecker
*Assistant Examiner* — Jae Woo
(74) *Attorney, Agent, or Firm* — Greenblum & Bernstein, P.L.C.

(57) ABSTRACT

To provide a method of producing an endoscope flexible tube and the like which can realize an endoscope with high insertability. A method of producing the endoscope flexible tube including: continuously discharging a liquid resin into a film shape from an annular discharge port surrounding an axis and a side surface of a cylindrical substrate; bringing the discharged film-shape resin into contact with the entire periphery of the substrate on the downstream side of the discharge port; covering a side surface of the substrate with the resin while moving the substrate in an axial direction to separate a portion where the resin and the substrate are in contact from the discharge port; and curing the resin covering the side surface of the substrate.

9 Claims, 10 Drawing Sheets

(51) Int. Cl.
*A61L 29/08* (2006.01)
*B29L 23/00* (2006.01)

(56) References Cited

U.S. PATENT DOCUMENTS

| | | | | |
|---|---|---|---|---|
| 2,544,915 | A | * | 3/1951 | Cameron ............ A61B 1/00195 228/173.6 |
| 3,460,975 | A | * | 8/1969 | Stebleton .................. A61F 2/00 427/2.24 |
| 3,574,996 | A | * | 4/1971 | Loos ..................... B29C 48/154 264/510 |
| 3,646,748 | A | * | 3/1972 | Lang ........................ E04C 5/08 57/7 |
| 3,837,773 | A | * | 9/1974 | Raley ..................... B29C 48/17 264/564 |
| 3,868,265 | A | * | 2/1975 | Sakai ..................... B05D 7/146 427/365 |
| 6,206,824 | B1 | | 3/2001 | Ohara et al. |
| 6,458,075 | B1 | * | 10/2002 | Sugiyama ............... B32B 5/028 600/140 |
| 7,044,906 | B2 | | 5/2006 | Hosoi et al. |
| 9,138,131 | B2 | | 9/2015 | Sato |
| 2005/0061381 | A1 | | 3/2005 | Hosoi et al. |
| 2009/0112066 | A1 | * | 4/2009 | Yago .................. A61B 1/00071 264/255 |
| 2010/0075075 | A1 | * | 3/2010 | Takahashi ............ A61B 1/0011 264/177.17 |
| 2010/0094086 | A1 | * | 4/2010 | Konstantin ........ A61B 1/00071 600/114 |
| 2010/0201029 | A1 | * | 8/2010 | Yago ...................... B29C 48/34 264/260 |
| 2011/0220270 | A1 | * | 9/2011 | Koori .................... B29C 48/919 156/144 |
| 2011/0295217 | A1 | * | 12/2011 | Tanaka ................ B29C 48/3366 264/209.8 |
| 2012/0053417 | A1 | | 3/2012 | Yamakawa et al. |
| 2015/0272424 | A1 | * | 10/2015 | Abe ............... B29C 48/18 600/140 |
| 2016/0024343 | A1 | | 1/2016 | Nakai et al. |

FOREIGN PATENT DOCUMENTS

| | | |
|---|---|---|
| JP | 2002-058637 A | 2/2002 |
| JP | 2011-067384 A | 4/2011 |
| JP | 2012-050557 A | 3/2012 |
| JP | 2014-188217 A | 10/2014 |
| JP | 2015-181903 A | 10/2015 |

* cited by examiner

METHOD OF PRODUCING ENDOSCOPE FLEXIBLE TUBE AND METHOD OF PRODUCING ENDOSCOPE

TECHNICAL FIELD

The present invention relates to a method of producing an endoscope flexible tube and a method of producing an endoscope.

BACKGROUND ART

A hardness adjuster described in Patent Literature 1 is proposed in order to enhance the insertability of an endoscope, that is, the ease of insertion.

CITATION LIST

Patent Literature

Patent Literature 1: JP 2012-050557 A

SUMMARY OF INVENTION

Technical Problem

However, the hardness adjuster described in Patent Literature 1 has a problem that the insertability of the endoscope is reduced if the use timing or the like is incorrect.

In one aspect, an object is to provide a method of producing an endoscope flexible tube and the like that can realize an endoscope with high insertability.

Solution to Problem

A method of producing an endoscope flexible tube including: continuously discharging a liquid resin into a film shape from an annular discharge port surrounding an axis and a side surface of a cylindrical substrate; bringing the discharged film-shape resin into contact with an entire periphery of the substrate on a downstream side of flow of the resin with respect to the discharge port; covering a side surface of the substrate with the resin while moving the substrate in an axial direction to separate a portion where the resin and the substrate are in contact from the discharge port; and curing the resin covering the substrate.

Advantageous Effects of Invention

In one aspect, it is possible to provide the method of producing the endoscope flexible tube and the like that can realize the endoscope with high insertability.

DESCRIPTION OF EMBODIMENTS

First Embodiment

Figure 1:
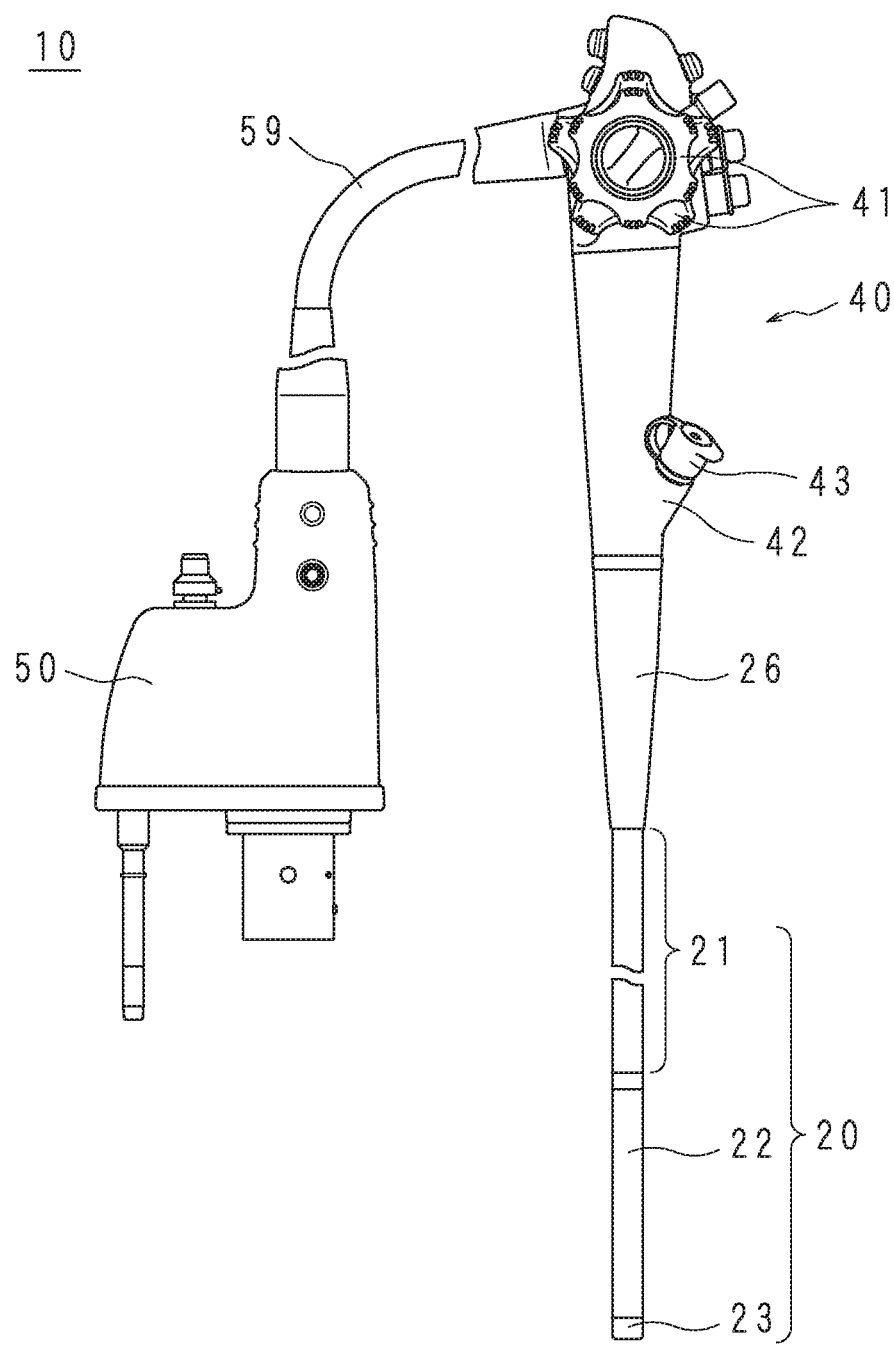
FIG. 1 is an exterior view of an endoscope.

FIG. 1 is an exterior view of an endoscope 10. An endoscope 10 of the present embodiment is a flexible scope for a lower gastrointestinal tract. The endoscope 10 includes an insertion unit 20, an operation unit 40, a universal cord 59, and a connector unit 50. The operation unit 40 has a bending knob 41 and a channel inlet 42. A forceps plug 43 having an insertion port to insert a treatment tool or the like is fixed to the channel inlet 42.

The insertion unit 20 is long and has one end connected to the operation unit 40 via a bend preventing portion 26. The insertion unit 20 includes a soft portion 21, a bending portion 22, and a distal end portion 23 in the order from the operation unit 40 side. The soft portion 21 is soft. A surface of the soft portion 21 is a tube-shaped flexible tube 30 (see FIG. 3). The bending portion 22 is bent according to an operation of the bending knob 41.

In the following description, a longitudinal direction of the insertion unit 20 is referred to as an insertion direction. Similarly, a side close to the operation unit 40 along the insertion direction is referred to as an operation unit side, and a side far from the operation unit 40 is referred to as a distal end side.

The universal cord 59 is long, and has a first end connected to the operation unit 40 and a second end connected to the connector unit 50. The universal cord 59 is soft. The connector unit 50 is connected to a video processor (not illustrated), a light source device, a display device, an air and water supply device, and the like.

Figure 2:
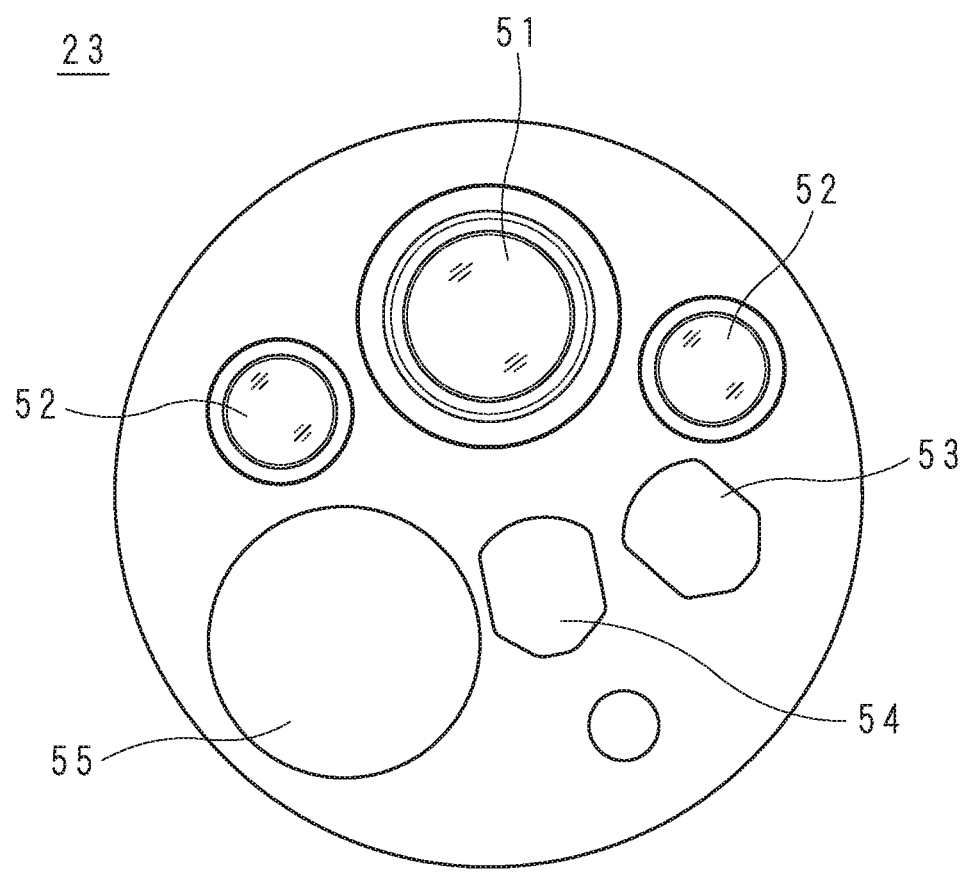
FIG. 2 is an external view of an end surface of a distal end portion.

FIG. 2 is an external view of an end surface of the distal end portion 23. An observation window 51, two illumination windows 52, an air supply nozzle 53, a water supply nozzle 54, a channel outlet 55, and the like are provided to an end surface of the distal end portion 23.

The end surface of the distal end portion 23 is substantially circular. The observation window 51 is provided above a center of the end surface in FIG. 2. The illumination windows 52 are provided on the left and right of the observation window 51. The air supply nozzle 53 and the water supply nozzle 54 are provided with outlets facing the observation window 51 at the lower right of the observation window 51. The channel outlet 55 is provided at the lower left of the observation window 51.

The description regarding the configuration of the endoscope 10 will be continued using FIGS. 1 and 2. A fiber bundle, a cable bundle, an air supply tube, a water supply tube, and the like are inserted inside the connector unit 50, the universal cord 59, the operation unit 40, and the insertion unit 20. The illumination light that has been emitted from the light source device is emitted from the illumination window 52 via the fiber bundle. A range illuminated by the illumination light is captured by an imaging element (not illustrated) via the observation window 51. A video signal is transmitted from the imaging element to the video processor via the cable bundle.

Air supplied from the air and water supply device is discharged from the air supply nozzle 53 toward the observation window 51 via the air supply tube. Similarly, water supplied from the air and water supply device is discharged from the water supply nozzle 54 toward the observation window 51 via the water supply tube. The air supply nozzle 53 and the water supply nozzle 54 are used, for example, to clean the observation window 51 during an endoscopy.

The channel inlet 42 and the channel outlet 55 are connected by a tube-shaped channel passing through each inside of the soft portion 21 and the bending portion 22. As a treatment tool (not illustrated) is inserted from the channel inlet 42, a distal end of the treatment tool can be caused to protrude from the channel outlet 55 to perform a procedure such as removal of a colorectal polyp.

Figure 3:
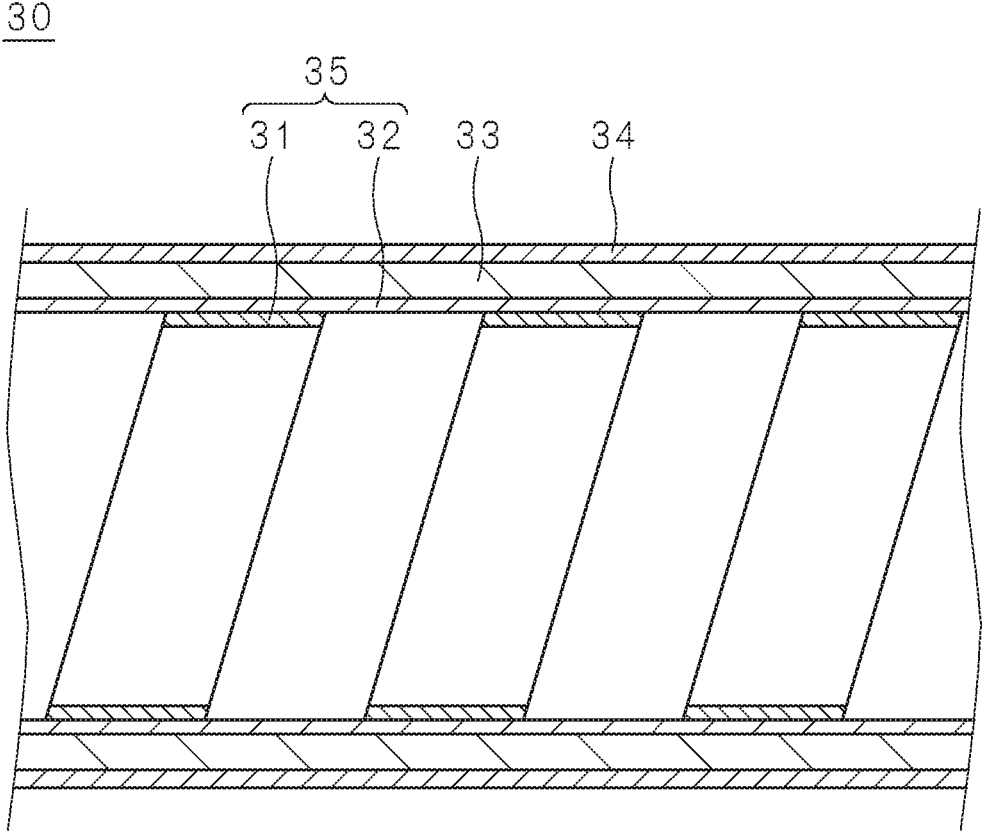
FIG. 3 is a cross-sectional view of a flexible tube.

FIG. 3 is a cross-sectional view of the flexible tube 30. As described above, the flexible tube 30 is an exterior member of the soft portion 21. FIG. 3 illustrates a cross section of the flexible tube 30 taken along the insertion direction.

The flexible tube 30 has a configuration in which the outer side of a spiral tube 31 obtained by spirally winding a strip-like metal is sequentially covered with a reticular tube 32, an outer sheath 33, and a top coat 34. The spiral tube 31 protects internal parts, such as the fiber bundle, the cable bundle, and various tubes, inserted therein when the soft portion 21 is bent.

The reticular tube 32 is formed by braiding a thin wire material. The thin wire material is, for example, a stainless-steel wire or a copper alloy wire. The thin wire material may be non-metal.

The outer sheath 33 is a resin layer molded on the outer side of the reticular tube 32. Examples of a material of the outer sheath 33 includes polyolefins such as an ethylene-vinyl acetate copolymer, fluorine-based resins such as polytetrafluoroethylene and an ethylene-tetrafluoroethylene copolymer, a polyester elastomer, a polyolefin elastomer, a fluorine elastomer, a polyurethane elastomer, a polyamide elastomer, silicone rubber, fluorine rubber, and the like. The outer sheath 33 may be a stacked body of a plurality of resin layers. A plurality of resin materials may be mixed to form the outer sheath 33.

The top coat 34 is, for example, a urethane resin or a fluorine resin. The top coat 34 protects the outer sheath 33 from a chemical solution or the like used for cleaning and disinfecting the endoscope 10.

A user of the endoscope 10 according to the present embodiment inserts the insertion unit 20 from the anus of a person to be examined. The user guides the distal end of the insertion unit 20 to a target site while observing a captured image through the observation window 51. At a part where the large intestine is strongly bent, the user operates the bending knob 41 to bend the bending portion 22 and performs an operation such as twisting the insertion unit 20 so as to advance the distal end portion 23 toward the cecum. The insertion unit 20 that has entered the inside of the large intestine is pushed against a wall of the large intestine and bent passively.

The insertability of the endoscope 10 is affected by the hardness of the insertion unit 20. The hardness of the insertion unit 20 is determined by the configuration of the flexible tube 30 and the configurations of the internal parts inserted into the flexible tube 30. The configurations of the internal parts are mainly determined based on the specifications of the endoscope 10 itself. Therefore, it is desirable that the entire insertion unit 20 have appropriate hardness by adjusting the configuration of the flexible tube 30.

Incidentally, the description is given by exemplifying the endoscope 10 for the lower gastrointestinal tract in the present embodiment as described above. The endoscope 10 for the lower gastrointestinal tract is long, and thus, whether the insertability is good or bad is greatly affected by the hardness of the insertion unit 20. Therefore, the lower gastrointestinal tract is a preferred application of the endoscope 10 of the present embodiment. However, the application of the endoscope 10 is not limited to the lower gastrointestinal tract. The application of the endoscope 10 may be an arbitrary application such as, for example, for an upper gastrointestinal tract, for a respiratory system, or for a urinary system.

Figure 4:
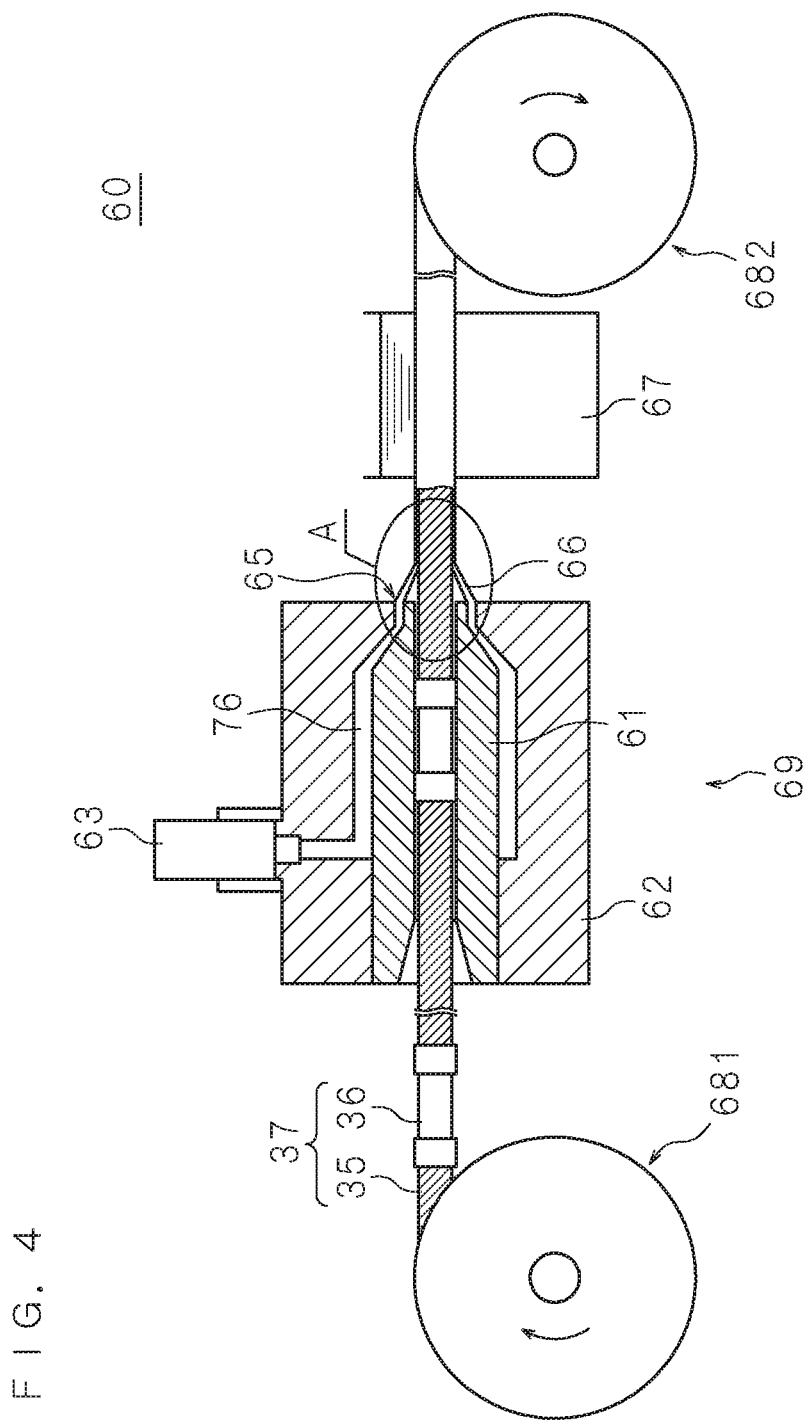
FIG. 4 is a schematic view of an outer sheath covering device.
Figure 5:
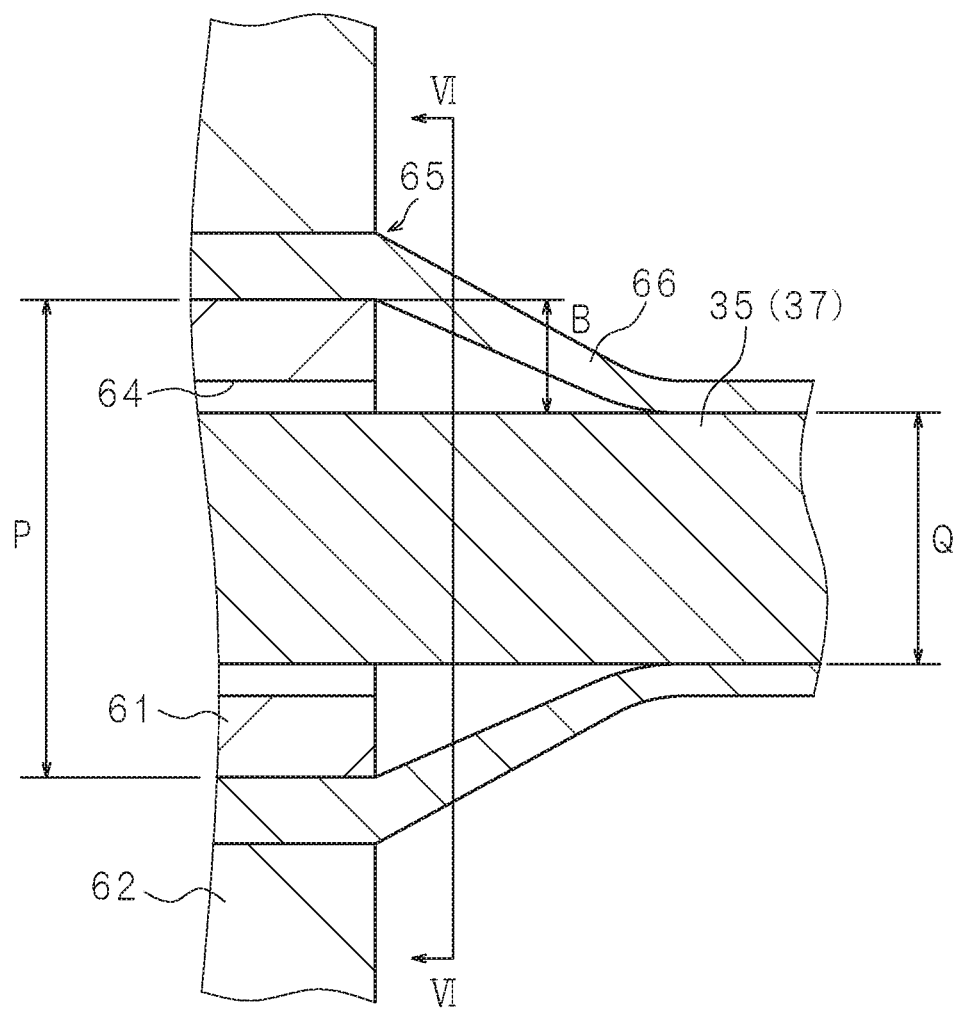
FIG. 5 is an enlarged view of a part A of FIG. 4.
Figure 6:
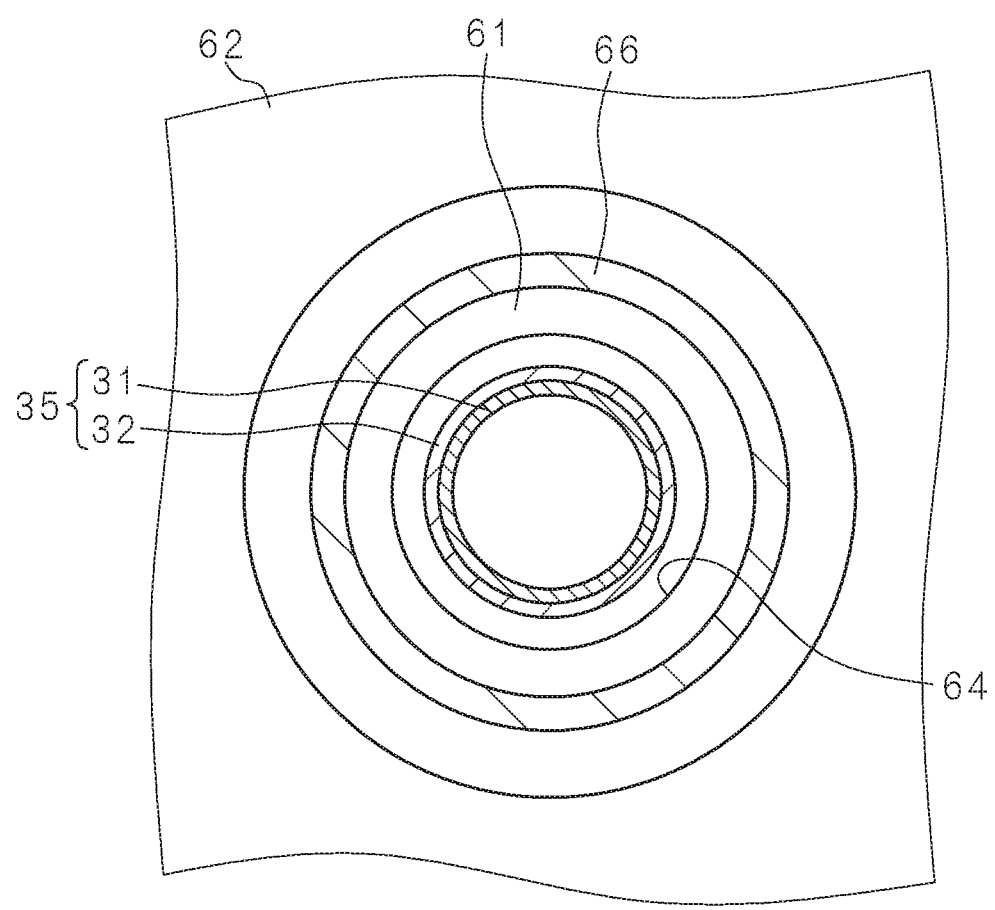
FIG. 6 is a cross-sectional view taken along the line VI-VI of FIG. 5.

FIG. 4 is a schematic view of an outer sheath covering device 60. FIG. 5 is an enlarged view of a part A of FIG. 4. FIG. 6 is a cross-sectional view taken along the line VI-VI of FIG. 5. The outer sheath covering device 60 is a device that covers a side surface of the substrate 35, obtained by covering the spiral tube 31 with the reticular tube 32, with the outer sheath 33. The outer sheath covering device 60 includes a molding unit 69 and a curing unit 67.

The molding unit 69 has a first mold 61, a second mold 62 and a raw material container 63. The first mold 61 has a substantially cylindrical shape having a substrate hole 64 penetrating along the central axis. The second mold 62 covers a side surface of the first mold 61. The raw material container 63 is connected to a flow path 76 provided between the first mold 61 and the second mold 62. The flow path 76 is continuous with an annular discharge port 65.

The outside of the discharge port 65 is under normal temperature and pressure. Details of the discharge port 65 will be described later. In the following description, an outer diameter of the first mold 61 at the discharge port 65 is denoted by P as illustrated in FIG. 5.

The raw material container 63 accommodates a resin 66 which is a raw material of the outer sheath 33. The resin 66 is a highly viscous liquid, and is extruded into the flow path 76 provided between the first mold 61 and the second mold 62 by an extrusion mechanism (not illustrated). Incidentally, when a thermoplastic resin is used for the outer sheath 33, the raw material container 63 may be provided with a heating mechanism which fuses a pellet-like raw material into a liquid. The raw material container 63 may have a mechanism for mixing a plurality of resin materials at a predetermined ratio.

The curing unit 67 cures the liquid resin 66. When the thermoplastic resin is used for the outer sheath 33, the curing unit 67 is a cooler. When an ultraviolet curing resin is used for the outer sheath 33, the curing unit 67 is an ultraviolet lamp. When a thermosetting resin is used for the outer sheath 33, the curing unit 67 is a heater.

The substrate 35 is produced for each of the endoscopes 10. In the following description, an outer diameter of the substrate 35 is denoted by Q as illustrated in FIG. 5. The plurality of substrates 35 are connected in a row by a connection member 36 to form a substrate-connected body 37. The substrate-connected body 37 is supplied in the state of being wound around a first drum 681.

The substrate-connected body 37 passes through the inside of the substrate hole 64 and is connected to a second drum 682 via the curing unit 67. As the first drum 681 and the second drum 682 rotate, the substrate-connected body 37 passes through the molding unit 69 and the curing unit 67 at a predetermined speed.

That is, the discharge port 65 is an annular shape surrounding the axis and the side surface of the substrate 35. The discharge port 65 is provided in the vicinity of a portion where the substrate 35 passes through the inside of the molding unit 69 and goes out of the molding unit 69, that is, at an end of the molding unit 69 on the downstream side of the flow of the substrate 35.

As illustrated in FIG. 5, a distance between an inner edge of the discharge port 65 and a surface of the substrate 35 is denoted by B. More specifically, half of a difference between the outer diameter P of the first mold 61 at the discharge port 65 and the outer diameter Q of the substrate 35 is the distance B.

The resin 66 extruded from the discharge port 65 through the flow path 76 forms a substantially conical film in contact with the substrate-connected body 37 at the top. The resin 66 maintains the state of the film by surface tension. As the first drum 681 and the second drum 682 rotate, the substrate-connected body 37 moves from the left to the right in FIG. 5, that is, a portion in which the substrate-connected body 37 and the film are in contact with each other moves in a direction away from the discharge port 65, whereby a surface of the substrate-connected body 37 is covered with the resin 66. The resin 66 is cured by the curing unit 67 to form the outer sheath 33.

That is, the discharge port 65 is provided at a portion where the resin 66 comes out of the molding unit 69, that is, at the end of the molding unit 69 on the downstream side of the flow of the resin 66. The resin 66 discharged from the discharge port 65 and the substrate-connected body 37 are separated by a distance indicated by B in FIG. 5. Therefore, there is a space between the resin 66 discharged from the discharge port 65 and the substrate 35, outside the molding unit 69.

Incidentally, an end surface of the first mold 61 and an end surface of the second mold 62 are disposed on the same plane in the vicinity of the discharge port 65 in FIG. 5, but the structure of the discharge port 65 is not limited thereto. For example, the end surface of the first mold 61 may protrude more than the end surface of the second mold 62. In addition, the end surface of the first mold 61 may be recessed more than the end surface of the second mold 62. In addition, any one or both of an outer peripheral surface of the first mold 61 and an inner peripheral surface of the second mold 62 in the portion in the vicinity of the discharge port 65 may be a tapered surface.

The substrate-connected body 37 which has passed through the curing unit 67 is wound around the second drum 682 as illustrated in FIG. 4, and introduced into the next producing process. Incidentally, the substrate-connected body 37 may be separated one by one by removing the connection member 36 instead of being wound around the second drum 682. The top coat 34 may be added between the curing unit 67 and the second drum 682.

Table 1 shows a relationship among the dimension B, a speed at which the substrate-connected body 37 passes through the molding unit 69, and a thickness of the outer sheath 33. The unit is mm.

TABLE 1

| B [mm] | Speed of Substrate-Connected Body [m/min] | | |
|---|---|---|---|
| | 0.3 | 0.6 | 1.0 |
| 1.0 | 0.30 | 0.15 | 0.08 |
| 3.0 | 1.00 | 0.50 | 0.25 |
| 5.0 | 1.60 | 0.80 | 0.40 |

As shown in Table 1, when the dimension B is constant, it is possible to make the outer sheath 33 thin by increasing the speed of the substrate-connected body 37. Similarly, when the speed of the substrate-connected body 37 is constant, it is possible to make the outer sheath 33 thicker by increasing the dimension B.

The hardness and thickness of the insertion unit 20 and the durability of the endoscope 10 are changed by changing the thickness of the outer sheath 33.

According to the present embodiment, the pressure is not applied when the substrate 35 is covered with the resin 66, the resin 66 does not easily enter a space between the thin wires constituting the reticular tube 32. Thus, it is possible to provide the flexible tube 30 with low hardness and flexibility. Since the soft flexible tube 30 is used, it is possible to provide the endoscope 10 with the soft insertion unit 20.

Furthermore, it is possible to change the thickness of the outer sheath 33 as described using Table 1, it is possible to provide the flexible tube 30 having desired hardness in accordance with the specifications of the endoscope 10. Therefore, it is possible to provide the method of producing the flexible tube 30 and the like which can realize the endoscope 10 with high insertability.

According to the present embodiment, it is possible to control the thickness of the outer sheath 33 by controlling the speed of the substrate-connected body 37. Therefore, it is possible to produce the flexible tubes 30 having different hardness using the same producing device. In addition, it is also possible to produce the flexible tube 30 in which hardness differs between the distal end side and the operation unit side. As a result, it is possible to provide the method of producing the flexible tube 30 and the like which can realize the endoscope 10 with higher insertability.

Incidentally, the flexible tube 30 may be used for the exterior of the universal cord 59. In this case, the substrate 35 may be, for example, a soft resin tube.

Second Embodiment

The present embodiment relates to a method of producing the flexible tube 30 having the outer sheath 33 having multiple layers. Descriptions regarding common parts with the first embodiment will be omitted.

Figure 7:
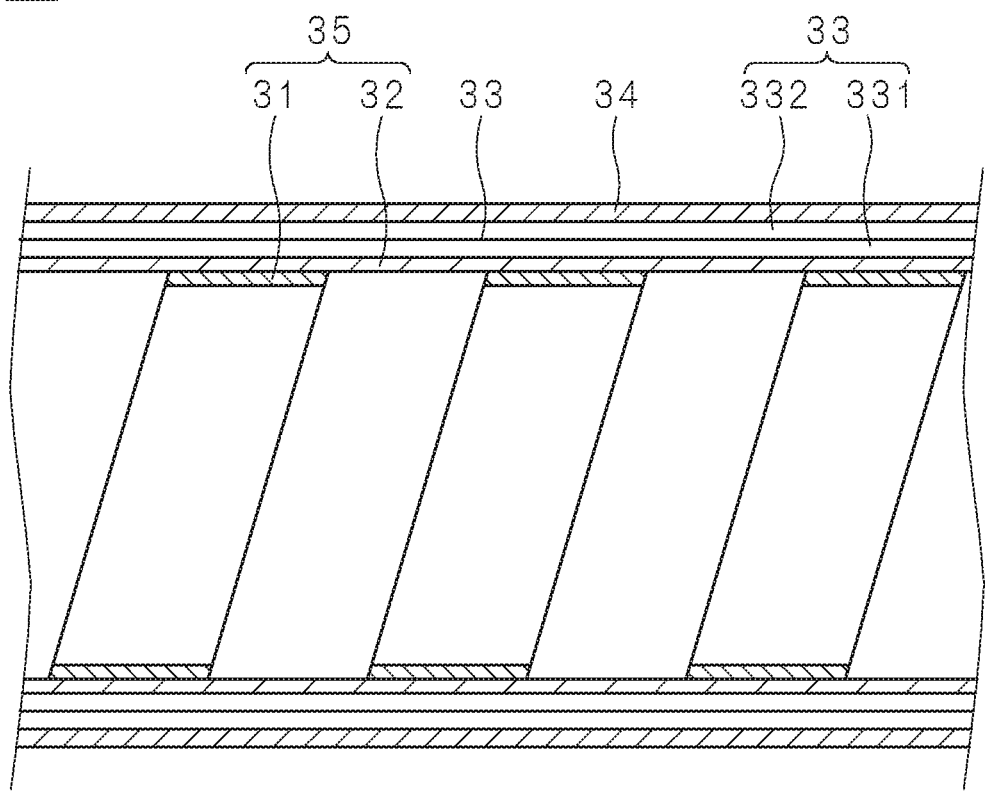
FIG. 7 is a cross-sectional view of a flexible tube of a second embodiment.

FIG. 7 is a cross-sectional view of the flexible tube 30 of a second embodiment. The outer sheath 33 has a two-layer structure of a first outer sheath 331 and a second outer sheath 332.

Both the first outer sheath 331 and the second outer sheath 332 are, for example, polyolefins such as ethylene-vinyl acetate copolymers, fluorine-based resins such as polytetrafluoroethylene and ethylene-tetrafluoroethylene copolymers, polyester elastomers, polyolefin elastomers, fluorine elastomers, polyurethane elastomers, polyamide elastomers, silicone rubber, fluorine rubber, and the like. The first outer sheath 331 and the second outer sheath 332 may be the same resin material or different resin materials.

For example, when a resin of the same type as the first outer sheath 331 and having a long molecular chain is used for the second outer sheath 332, it is possible to make the second outer sheath 332 harder than the first outer sheath 331 and firmly bond the both. Since the flexible tube 30 having the above outer sheath 33 is used, it is possible to provide the endoscope 10 with high insertability.

Figure 8:
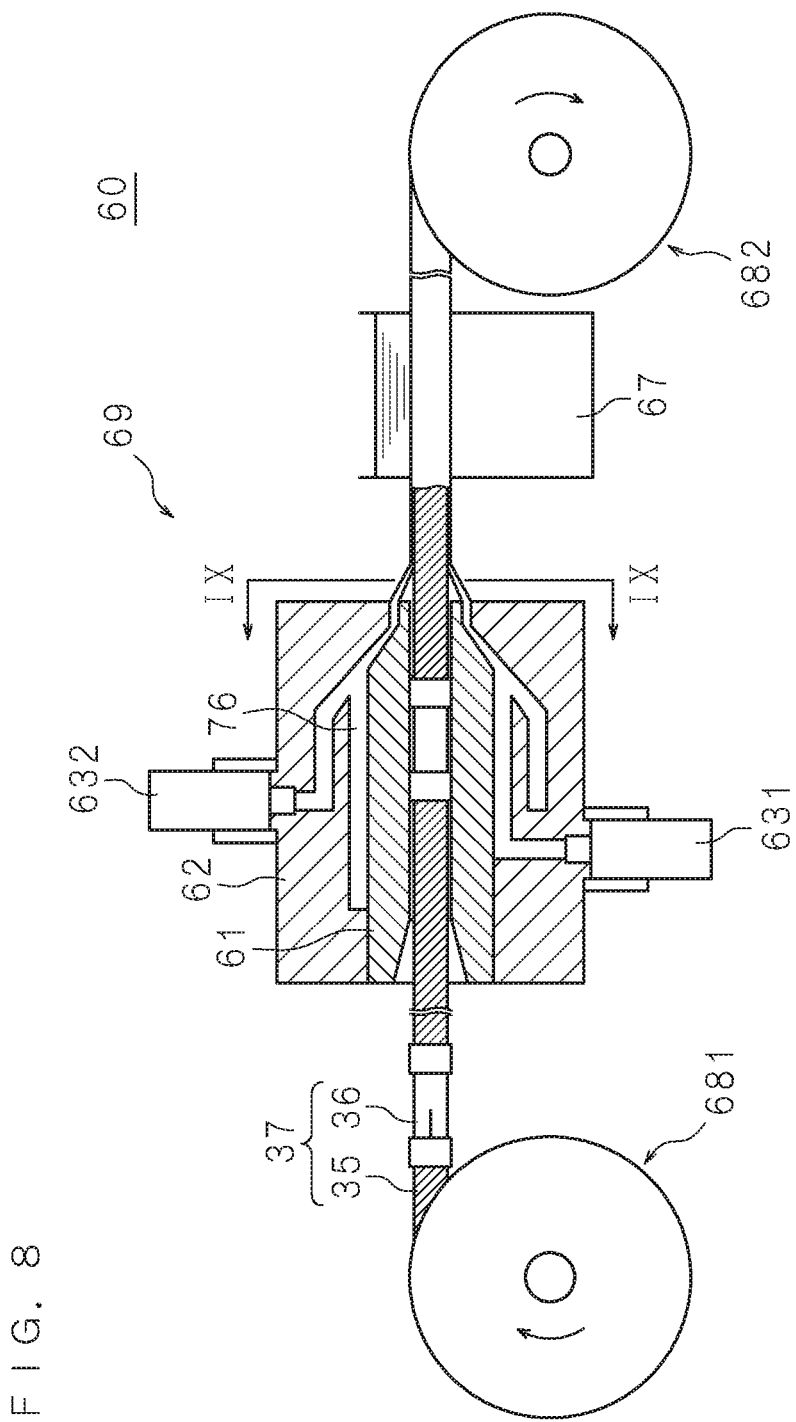
FIG. 8 is a schematic view of an outer sheath covering device of the second embodiment.
Figure 9:
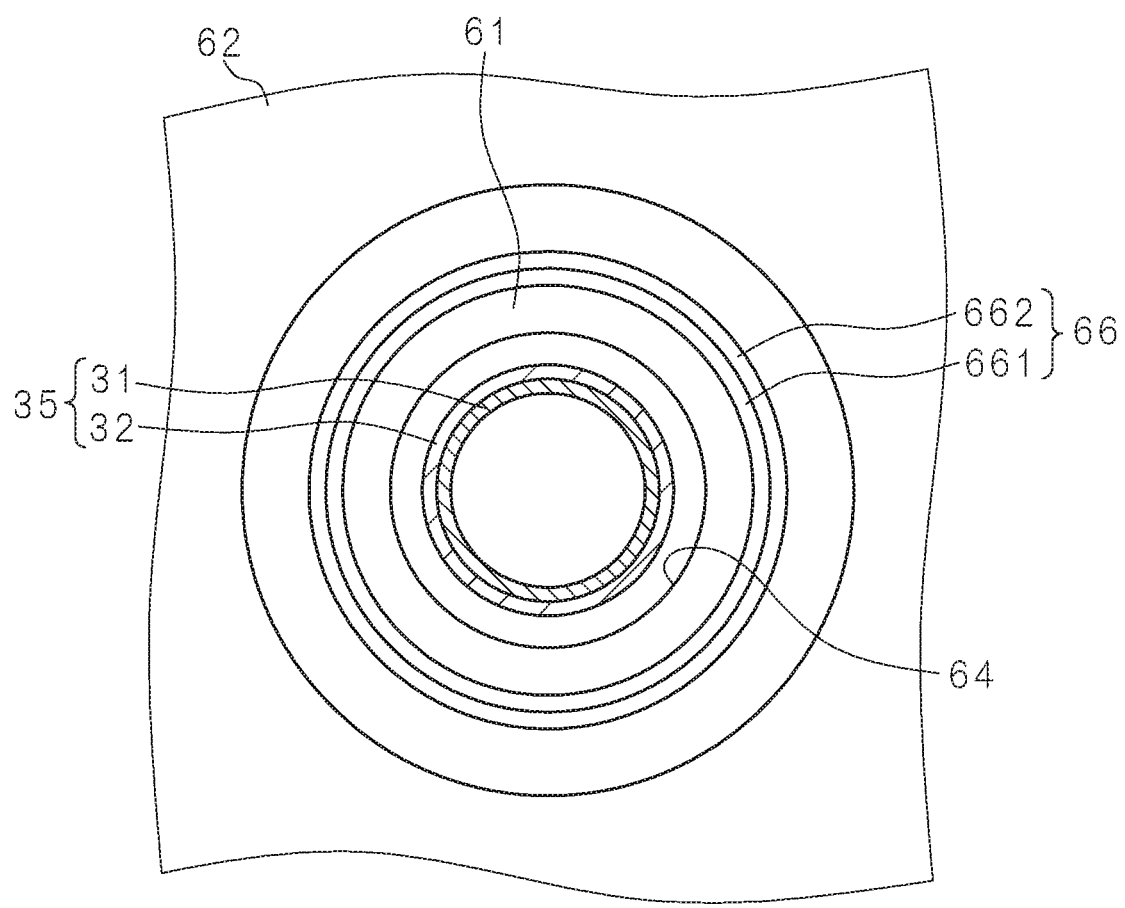
FIG. 9 is a cross-sectional view taken along line IX-IX in FIG. 8.

FIG. 8 is a schematic view of the outer sheath covering device 60 of the second embodiment. FIG. 9 is a cross-sectional view taken along line IX-IX of FIG. 8. The outer sheath covering device 60 includes a first raw material container 631 and a second raw material container 632.

In the first raw material container 631, a first resin 661 which is a raw material of the first outer sheath 331 is accommodated. In the second raw material container 632, a second resin 662 which is a raw material of the second outer sheath 332 is accommodated.

The first raw material container 631 is connected to the flow path 76. The second raw material container 632 is connected to the outer peripheral side of the flow path 76 at the downstream side of flow of the first resin 661 supplied from the first raw material container 631 to the flow path 76. Thus, a film having a two-layer structure in which the second resin 662 covers the outer periphery of the first resin 661 is formed as illustrated in FIG. 9.

As the substrate-connected body 37 moves from left to right in FIG. 5, a surface of the substrate-connected body 37 is covered with the first resin 661 and the second resin 662 in two layers. The first resin 661 and the second resin 662 are cured by the curing unit 67 to form the first outer sheath 331 and the second outer sheath 332.

The outer sheath covering device 60 may be provided with three or more raw material containers 63, and may produce the flexible tube 30 having three or more layers of the outer sheaths 33.

According to the present embodiment, it is possible to provide the flexible tube 30 having the multi-layer outer sheath 33. Since the flexible tube 30 of the present embodiment is used, it is possible to provide the endoscope 10 with high insertability. In addition, it is possible to provide the endoscope 10 with higher insertability by covering the substrate 35 while changing a resin ratio between the first resin 661 and the second resin 662.

The same raw material may be accommodated in the first raw material container 631 and the second raw material container 632. When one of the raw material containers 63 becomes empty, it is possible to replenish the raw material without stopping the outer sheath covering device 60.

Third Embodiment

The present embodiment relates to the outer sheath covering device 60 provided with a suction chamber 75. Descriptions regarding common parts with the first embodiment will be omitted.

Figure 10:
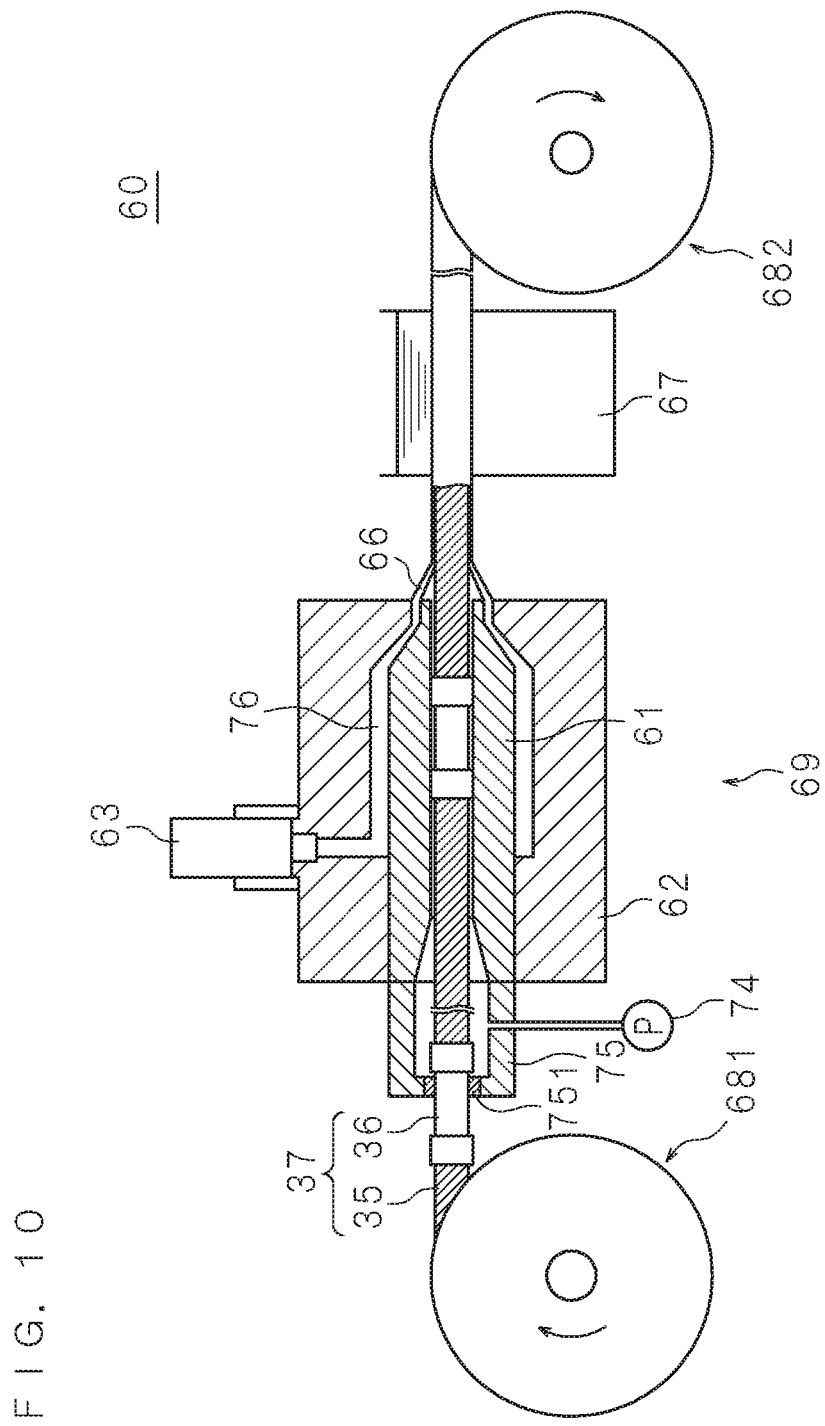
FIG. 10 is a schematic view of an outer sheath covering device of a third embodiment.

FIG. 10 is a schematic view of the outer sheath covering device 60 of a third embodiment. The outer sheath covering device 60 has the suction chamber 75 at an inlet where the substrate-connected body 37 enters the first mold 61. A valve 751 is provided at an inlet of the suction chamber 75. The substrate-connected body 37 penetrates the valve 751. The suction chamber 75 is connected to a pump 74.

The pump 74 forms a negative pressure inside the suction chamber 75. The substrate 35 constituting the substrate-connected body 37 is the structure in which the spiral tube 31 is covered with the reticular tube 32 as described above, and thus, has air permeability. Thus, a side surface of the substrate 35 that is not covered with the resin has a negative pressure as compared to a surface of the cured resin 66. Thus, the film-shape resin 66 is sucked and brought into close contact with the reticular tube 32.

According to the present embodiment, it is possible to provide the flexible tube 30 in which the reticular tube 32 and the outer sheath 33 are in close contact with each other and hardly peeled off.

The suction chamber 75 may be provided with a pressure sensor. When a hole is opened in the substantially conical film formed of the resin 66, the pressure inside the suction chamber 75 rapidly rises, and thus, can be easily detected. As a result, it is possible to detect an abnormality of the outer sheath covering device 60 early.

It is possible to control the degree of close contact between the reticular tube 32 and the outer sheath 33 by controlling the pressure inside the suction chamber 75. The flexible tube 30 can be made hard by increasing the degree of close contact between the reticular tube 32 and the outer sheath 33. Therefore, it is possible to produce the flexible tubes 30 having different hardness using the same producing device. In addition, it is also possible to produce the flexible tubes 30 in which the degree of close contact between the reticular tube 32 and the outer sheath 33 differs between the distal end side and the operation unit side. As a result, it is possible to provide the method of producing the flexible tube 30 and the like which can realize the endoscope 10 with higher insertability.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the present invention is defined not by the above-described meaning but by claims, and intends to include all modifications within meaning and a scope equal to claims.

Regarding the embodiments including the first to third embodiments, the following appendixes are additionally disclosed.

(Supplementary Note 1)

A method of producing an endoscope flexible tube 30, the method including:

continuously discharging a liquid resin 66 into a film shape from an annular discharge port 65 surrounding an axis and a side surface of a cylindrical substrate 35;

bringing the discharged film-shape resin 66 into contact with an entire periphery of the substrate 35 on a downstream side of flow of the resin with respect to the discharge port 65;

covering a side surface of the substrate 35 with the resin 66 while moving the substrate 35 in an axial direction to separate a portion where the resin 66 and the substrate 35 are in contact from the discharge port 65; and curing the resin 66 covering the substrate 35.

(Supplementary Note 2)

The method of producing the endoscope flexible tube 30 described in Supplementary Note 1, wherein the resin 66 is in a state where a plurality of resin materials are stacked.

(Supplementary Note 3)

The method of producing the endoscope flexible tube 30 described in Supplementary Note 1 or 2, wherein a space is present between the resin 66 discharged from the discharge port and the substrate 35.

(Supplementary Note 4)

The method of producing the endoscope flexible tube 30 described in any one of Supplementary Notes 1 to 3, wherein the substrate 35 has air permeability on a side surface, and a side surface of the substrate 35, which is not covered by the resin, is set to a negative pressure as compared to a surface of the cured resin 66.

(Supplementary Note 5)

The method of producing the endoscope flexible tube 30 described in any one of Supplementary Notes 1 to 4, wherein
the resin 66 is a thermoplastic resin, and
the substrate 35 has a spiral tube 31, obtained by spirally winding a metal plate, and a reticular tube 32 covering an outer side of the spiral tube 31.

(Supplementary Note 6)

A method of producing an endoscope 10, the method including:
continuously discharging a liquid resin 66 into a film shape from an annular discharge port 65 surrounding an axis and a side surface of a cylindrical substrate 35;
bringing the discharged film-shape resin 66 into contact with an entire periphery of the substrate 35 on a downstream side of flow of the resin with respect to the discharge port 65;
covering a side surface of the substrate 35 with the resin 66 while moving the substrate 35 in an axial direction to separate a portion where the resin 66 and the substrate 35 are in contact from the discharge port 65; and
using an endoscope flexible tube 30, produced by curing the resin 66 covering the side surface of the substrate 35, for an exterior of an insertion unit 20.

REFERENCE SIGNS LIST 10 endoscope
20 insertion unit
21 soft portion
22 bending portion
23 distal end portion
26 bend preventing portion
30 flexible tube (endoscope flexible tube)
31 spiral tube
32 reticular tube
33 outer sheath
331 first outer sheath
332 second outer sheath
34 top coat
35 substrate
36 connection member
37 substrate-connected body
40 operation unit
41 bending knob
42 channel inlet
43 forceps plug
50 connector unit
51 observation window
52 illumination window
53 air supply nozzle
54 water supply nozzle
55 channel outlet
59 universal cord
60 outer sheath covering device
61 first mold
62 second mold
63 raw material container
631 first raw material container
632 second raw material container
64 substrate hole
65 discharge port
66 resin
661 first resin
662 second resin
67 curing unit
681 first drum
682 second drum
69 molding unit
74 pump
75 suction chamber
751 valve
76 flow path

The invention claimed is:

1. A method of producing an endoscope flexible tube, the method comprising:
continuously discharging a resin in a liquid state into a film shape from an annular discharge port surrounding an axis and a side surface of a cylindrical substrate having air permeability on the side surface;
bringing the resin discharged into the film shape into contact with an entire periphery of the substrate on a downstream side of flow of the resin with respect to the discharge port;
covering a side surface of the substrate with the resin while moving the substrate in an axial direction to separate a portion where the resin and the substrate are in contact from the discharge port;
setting pressure surrounding a side surface of the substrate, which is not covered by the resin, to a negative pressure as compared to a surface of the resin in a cured state;
detecting when a hole is opened in the resin discharged into the film shape based on a pressure at an area set to the negative pressure; and
curing the resin covering the substrate.

2. The method of producing the endoscope flexible tube according to claim 1, wherein
the resin is in a state where a plurality of resin materials are stacked.

3. The method of producing the endoscope flexible tube according to claim 2, wherein
the resin is a thermoplastic resin, and
the substrate has a spiral tube, obtained by spirally winding a metal plate, and a reticular tube covering an outer side of the spiral tube.

4. The method of producing the endoscope flexible tube according to claim 2, wherein
a space is present between the resin discharged from the discharge port and the substrate.

5. The method of producing the endoscope flexible tube according to claim 4, wherein
the resin is a thermoplastic resin, and
the substrate has a spiral tube, obtained by spirally winding a metal plate, and a reticular tube covering an outer side of the spiral tube.

6. The method of producing the endoscope flexible tube according to claim 1, wherein
a space is present between the resin discharged from the discharge port and the substrate.

7. The method of producing the endoscope flexible tube according to claim 6, wherein
the resin is a thermoplastic resin, and
the substrate has a spiral tube, obtained by spirally winding a metal plate, and a reticular tube covering an outer side of the spiral tube.

8. The method of producing the endoscope flexible tube according to claim 1, wherein
the resin is a thermoplastic resin, and
the substrate has a spiral tube, obtained by spirally winding a metal plate, and a reticular tube covering an outer side of the spiral tube.

9. A method of producing an endoscope, the method comprising:

continuously discharging a resin in a liquid state into a film shape from an annular discharge port surrounding an axis and a side surface of a cylindrical substrate having air permeability on the side surface;

bringing the resin discharged into the film shape into contact with an entire periphery of the substrate on a downstream side of flow of the resin with respect to the discharge port;

covering a side surface of the substrate with the resin while moving the substrate in an axial direction to separate a portion where the resin and the substrate are in contact from the discharge port;

setting pressure surrounding a side surface of the substrate, which is not covered by the resin, to a negative pressure as compared to a surface of the resin in a cured state;

detecting when a hole is opened in the resin discharged into the film shape based on a pressure at an area set to the negative pressure;

producing an endoscope flexible tube by curing the resin covering the side surface of the substrate; and using the endoscope flexible tube for an exterior of an insertion unit.

* * * * *